(12) United States Patent
Oda

(10) Patent No.: US 6,548,656 B1
(45) Date of Patent: Apr. 15, 2003

(54) FRAME ADJUST LINKERS

(75) Inventor: Toshiaki Oda, Shizuoka (JP)

(73) Assignee: Japan Science and Technology Corporation, Saitama (JP)

( * ) Notice: Subject to any disclaimer, the term of this patent is extended or adjusted under 35 U.S.C. 154(b) by 0 days.

(21) Appl. No.: 09/914,445

(22) PCT Filed: Dec. 28, 1999

(86) PCT No.: PCT/JP99/07393

§ 371 (c)(1),
(2), (4) Date: Nov. 26, 2001

(87) PCT Pub. No.: WO01/48226

PCT Pub. Date: Jul. 5, 2001

(51) Int. Cl.⁷ .......................... C12N 15/11; C07H 21/04
(52) U.S. Cl. ..................... 536/24.2; 536/23.1; 536/24.1
(58) Field of Search ............................... 536/23.1, 24.1, 536/24.2

(56) References Cited

FOREIGN PATENT DOCUMENTS

JP          63-294790          12/1988

OTHER PUBLICATIONS

Perlman and Halvorson, The MURFI linker for multiple reading frame insertion of a sense or nonsense codon into DNA Nucleic Acids Res. Mar. 11, 1986; 14(5):2139–55.*

M. Broeker et al., "PUC–12–stop an expression vector with portable translation stop signals", BIOSIS No. 81072068 & Appln. Microbiol. Biotechnol. (1986), vol. 23, Nos. 3–4, pp. 294–296.

R. F. Pettersson et al., "Chemical Synthesis and Molecular of a stop oligo necleotide encoding UGA translation terminator in all 3 reading frames", BIOSIS NO. 77067082 & Gene (1983), vol. 24, No. 1, pp. 15–28.

\* cited by examiner

Primary Examiner—James Ketter
Assistant Examiner—Daniel Sullivan
(74) Attorney, Agent, or Firm—Wenderoth, Lind & Ponack, L.L.P.

(57) ABSTRACT

This application provides frame-adjusting linkers FAL-1 and FAL-2 which are single-stranded DNA consisting of a palindrome base sequence of SEQ ID NO. 1 and SEQ ID NO. 2, respectively. These linkers are able to prepare mutant DNA sequences having correct translation frames before and behind the any cleaved sites, therefore, time and cost for preparation of mutant protein, etc. can be greatly reduced.

4 Claims, 5 Drawing Sheets

Frame Adjust Linker-1 (FAL-1)

Fig. 5

Frame Adjust Linker-1 (FAL-1)

```
 1 2 3 1 2 3 1 2 3 1 2 3
 G C C G G C G C C G G C
 ─────────     ─────────
   NaeI           NaeI
  (3, 3)         (3, 3)

NgoMIV         NgoMIV
  (2, 1)         (2, 1)

─────────────
            BbeI
           (1, 2)
```

Fig. 6

Frame Adjust Linker-2 (FAL-2)

```
    2 3 1 2 3 1 2 3 1 2 3 1 2 3
 5' G C C C G G G C C C G G G C  3'
    ─────────       ─────────
      SmaI             SmaI
         ───────────────
              ApaI
             Bsp1201
```

FRAME ADJUST LINKERS

This applicaiton is a U.S. National stage of International Application No. PCT/JP99/07393 filed Dec. 28, 1999.

TECHNICAL FIELD

The invention of this application relates to a linker that is able to adjust the translation frame of DNA chain encoding protein. More particularly, it relates to a frame-adjusting linker that is indispensable for various modification of DNA fragments.

BACKGROUND ART

Protein is synthesized (translated) in vivo from a messenger RNA (mRNA) transcribed from genomic DNA. For analyzing function of a protein in the area of molecular biology and life science, it is general to express a mutant protein from a mutant DNA fragment prepared by transferring information of mRNA to DNA to give a double-stranded DNA and operating the base sequence of this DNA fragment (cDNA).

In the preparation of deletion or insertion mutant DNA fragment, it is usually carried out that two sites of DNA are cleaved by restriction enzymes to remove the sequence between them or that one site is cleaved and some sequence or base is inserted thereinto.

DNA strand encodes one amino acid residue by a block (codon) of three bases. Therefore, when DNA is cleaved by a restriction enzyme so that a part of sequence or base is deleted or when some sequence or base is inserted to the cleaved site, there is a risk that frame of the codon changes and, as a result, the amino acid sequence of the protein in the C-terminal side from the mutated site is changed to a completely different sequence. Or it is also probable that a stop codon is formed therein and the synthesis of protein is interrupted. In this case, the desired mutant protein cannot be prepared. Therefore, when a mutation such as deletion or addition is introduced into DNA strand, it is necessary to make the translation frame in sequence before and behind the mutation being same.

In general, a linker DNA consisting of double-stranded oligonucleotide is linked at the cleaved site for adjusting the translation frames. However, it is necessary to prepare various kinds of linkers for each time depending upon the type of the restriction enzyme used and, in addition, selection of the linker is not always easy. Therefore, a lot of labor is needed for the preparation of the mutant DNA fragment having correct translation frame.

DISCLOSURE OF INVENTION

The invention of this application has been carried out in view of the circumstances of the prior art as mentioned above. The object of the invention is to provide a frame-adjusting linker, which has the sites recognized by plural restriction enzymes, for the preparation of mutant DNA sequences having the correct translation frames before and behind the any cleavage sites.

As a solution for the above-mentioned object, this application provides the following inventions (1) to (4).

(1) A translation frame-adjusting linker, which is a single-stranded DNA consisting of a palindrome base sequence of SEQ ID NO. 1.

(2) The translation frame-adjusting linker claim 1, of which the 5'-terminal is phosphorylated.

(3) A translation frame-adjusting linker, which is a single-stranded DNA consisting of a palindrome base sequence of SEQ ID NO. 2.

(4) The translation frame-adjusting linker of claim 3, of which the 5'-terminal is phosphorylated.

BRIEF EXPLANATION OF THE DRAWINGS

FIG. 5 shows translation frames of cross section of the cleaved parts by various restriction enzymes in FAL-1.

FIG. 6 shows base sequence, restriction enzyme-recognizing sequence (underlined) and translation frames (1,2,3) of the frame-adjusting linker FAL-2 of this invention (SEQ ID NO: 2).

BEST MODE FOR CARRYING OUT THE INVENTION

Figure 1:
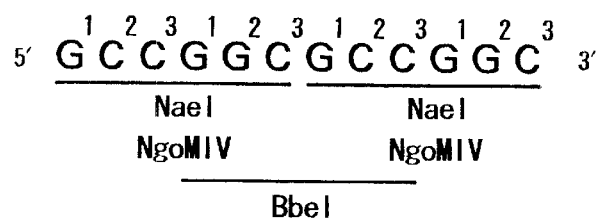
FIG. 1 shows base sequence, restriction enzyme-recognizing sequence (underlined) and translation frames (1,2,3) of the frame-adjusting linker FAL-1 of this invention (SEQ ID NO: 1).

The frame-adjusting linker according to the invention (1) of this applicaiton is a single-stranded DNA consisting of a palindrome base sequence of SEQ ID NO. 1. Hereinafter, the frame-adjusting linker of the invention (1) may be referred to FAL-1. FIG. 1 shows base sequence, restriction enzyme-recognizing sequence (underlined) and translation frames (1,2,3) of this FAL-1. As shown in FIG. 1, two sequences of "GCCGGC", cleavable by the restriction enzymes Nae I and NgoM IV, are connected in FAL-1. This FAL-1 also has a sequence "GGCGCC", cleavalbe by the restriction enzyme Bbe I. As hereunder, cleavages of the FAL-1 by these restriction enzymes will be illustrated.

Cleavage by Nea I

Figure 2:
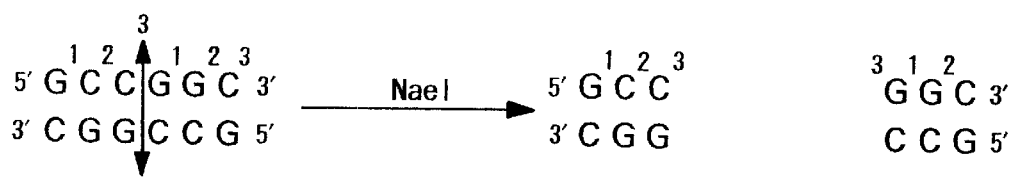
FIG. 2 shows a sequence of the cleaved part when FAL-1 is treated with a restriction enzyme Nae I.

The sequences "GCCGGC" at the right and left sides of FAL-1 are cleaved by Nae I as shown in FIG. 2 and the resulting cleaved parts are blunt ends. Fragments at right and left sides after the cleavage finish with the translation frame 3 and then start with the translation frame 3. Hereinafter, the translation frame to finish and start of the sequence after the cleavage is referred to (3,3).

Cleavage by NgoM IV

Figure 3:
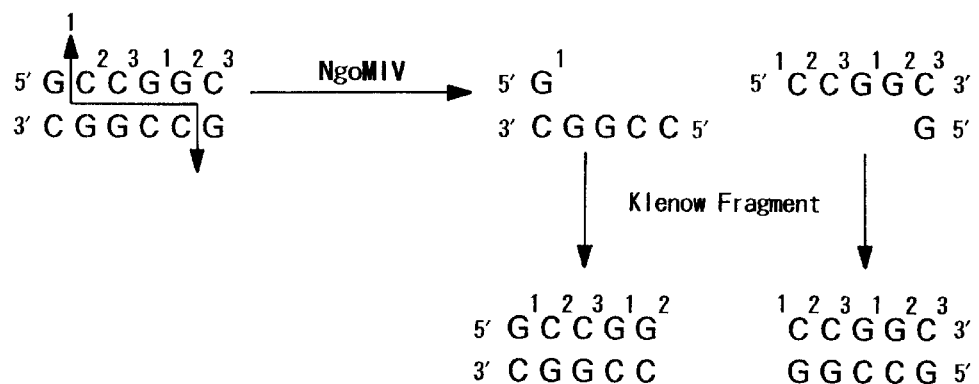
FIG. 3 shows a sequence of the cleaved part when FAL-1 is treated with a restriction enzyme NgoM IV and then treated with a Klenow fragment of DNA polymerase I.

The restriction enzyme NgoM IV recognizes "GCCGGC" which is the same sequence as the above Nae I does although their cleaving sites are different. the sequences "GCCGGC" at right and left sides of FAL-1 are cleaved by NgoM IV as shown in FIG. 3. This cleaved part becomes a 5'-protruding end and, when it is blunt-ended by treating with a Klenow fragment, the DNA fragment finishes with a translation frame 2 and then starts with a translation frame 1 as shown in FIG. 3 (2,1).

Cleavage by Bbe I

Figure 4:
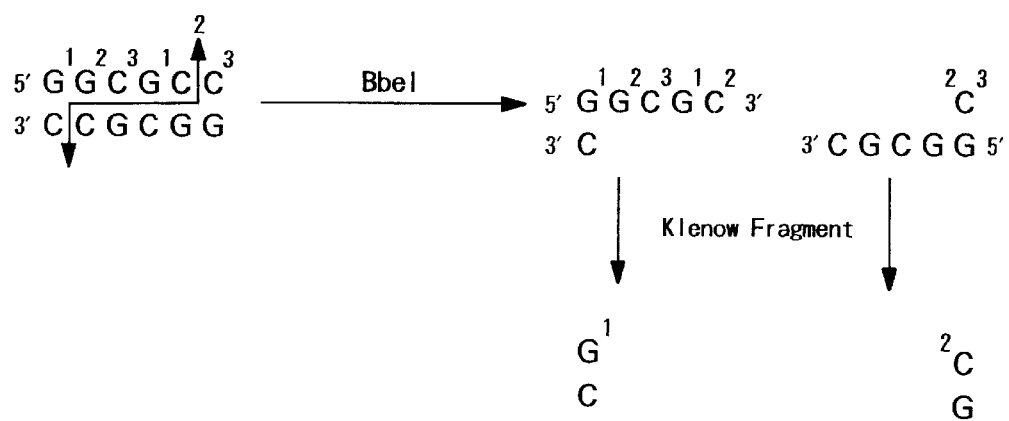
FIG. 4 shows a sequence of the cleaved part when FAL-1 is treated with a restriction enzyme Bbe I and then treated with a Klenow fragment.

The sequence "GGCGCC" of FAL-1 is cleaved by the restriction enzyme Bbe I as shown in FIG. 4 and its cleaved part becomes a 3'- protruding end. When it is blunt-ended by a Klenow fragment, the section becomes (1,2) as shown in FIG. 4.

FIG. 5 shows the cleaved parts by each of the restriction enzyme in FAL-1 and the translation frames after the cleavage. Accordingly, when this frame-adjusting linker FAL-1 is ligated to one end of the DNA fragment, digested with one of three kinds of restriction enzymes and then blunt-ended using a Klenow fragment, it is possible to finish the DNA fragment of 3'-terminal with the translation frame 1 (using Bbe I), the translation frame 2 (using NgoM IV) or the translation frame 3 (using Nae I). In addition, it is possible to initiate the 5'-terminal of DNA with the translation frame 1 (using NgoM IV), the translation frame 2 (using Bbe I) or the translation frame 3 (using Nae I).

Now, the frame-adjusting linker (FAL-2) of the invention (3) will be illustrated.

The FAL-2 is a single-stranded DNA consisting of a palindrome base sequence of SEQ ID NO. 2. In the FAL-2, two sequences of "CCCGGG", cleavable by the restriction enzyme Sma I, are connected and, in addition, there are each one "G" and "C" at the 5'-side and 3'-side, respectively, as shown in FIG. 6. The FAL-2 also has the sequence "GGGCCC", cleavable by the restriction enzymes Apa I and Bsp 120I. As hereinunder, the cleavage of FAL-2 by these restriction enzymes will be illustrated.

Cleavage by Sma I

Figure 7:
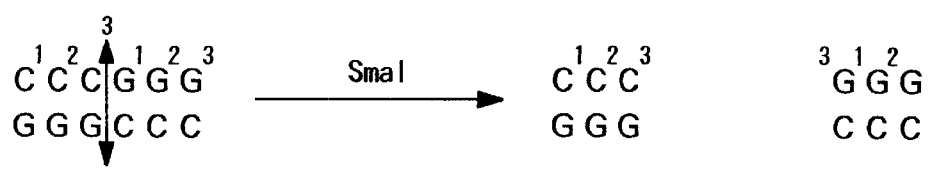
FIG. 7 shows a sequence of the cleaved part when FAL-2 is treated with a restriction enzyme Sma I.

The sequences "CCCGGG" at right and left sides of FAL-2 are cleaved by Sma I as shown in FIG. 7 and the resulting section become blunt ends. Fragments at right and left sides after the cleavage finish with the translation frame 3 and then start with the translation frame 3 (3,3).

Cleavage by Apa I

Figure 8:
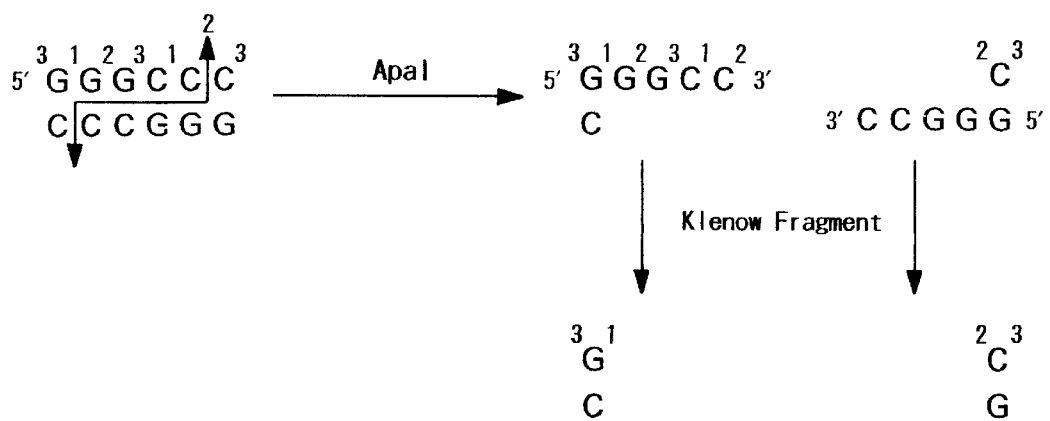
FIG. 8 shows a sequence of the cleaved part when FAL-2 is treated with a restriction enzyme Apa I and then treated with a Klenow fragment.

The sequence "GGGCCC" of FAL-2 is cleaved by the restriction enzyme Apa I as shown in FIG. 8 and its cleaved part becomes a 3'-protruding end. When it is blunt-ended by a Klenow fragment, the section becomes (1,2) as shown in FIG. 8.

Cleavage by Bsp 120I

Figure 9:
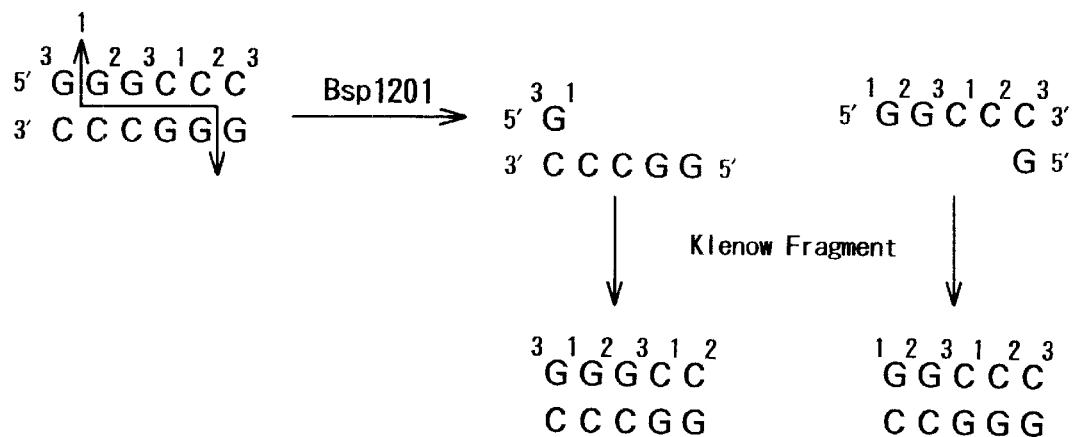
FIG. 9 shows a sequence of the cleaved part when FAL-2 is treated with a restriction enzyme Bsp 120I and then treated with a Klenow fragment.

The sequence "GGGCCC" of FAL-2 is cleaved by the restriction enzyme Bsp 120I as shown in FIG. 9 and its cleaved part becomes a 5'-protuding end. When it is blunt-ended by a Klenow fragment, the section becomes (2,1) as shown in FIG. 9.

Figure 10:
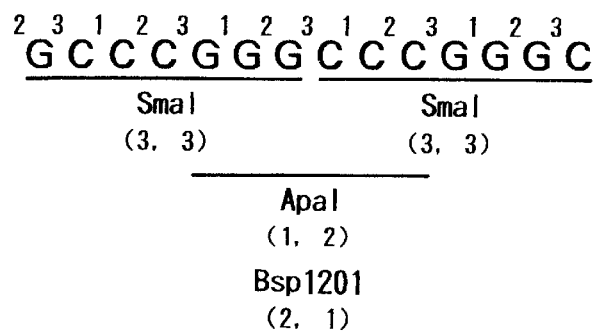
FIG. 10 shows translation frames of cross section of the cleaved parts by various restriction enzymes in FAL-2.

FIG. 10 shows the cleaved parts by each of the restriction enzyme in FAL-2 and translation frames after the cleavage. Accordingly, when this frame-adjusting linker FAL-2 is ligated to one end of a DNA fragment, digested with one of three kinds of restriction enzymes and then blunt-ended using a Klenow fragment, it is possible to finish the DNA fragment of 3'-terminal with the translation frame 1 (using Apa I), the translation frame 2 (using Bsp 120I) or the translation frame 3 (using Sma I). In addition, it is possible to initiate the 5'-terminal of DNA with the translation frame 1 (using Bsp 120I), the translation frame 2 (using Apa I) or the translation frame 3 (using Sma I).

As mentioned above, when the frame-adjusting linkers FAL-1 and FAL-2 provided by this applicaiton are combined in various manners and also the six kinds of restriction enzymes recognizing the sequence of each linker are appropriately selected and used, it is now possible to prepare variant DNA sequences having correct translation frames before and behind the mutation sites.

Incidentally, it is preferred that the 5'-terminal of the frame-adjusting linker of this invention is previously phosphorylated. As a result, these linkers can be ligated directly DNA fragment without 5'-phosphorylation by a polynucleotide kinase.

INDUSTRIAL APPLICABILITY

The frame-adjusting linker of this invention can be utilized in preparing a mutant DNA fragment for the production of mutant protein which is useful, for example, in a field of fundamental research area such as biology and medicine or in an area of research and development of pharmaceuticals and food processing.

What is claimed is:

1. A translation frame-adjusting linker, which is a single-stranded DNA consisting of the palindromic base sequence of SEQ ID NO: 1.

2. The translation frame-adjusting linker of claim 1, of which the 5'-terminal is phosphorylated.

3. A translation frame-adjusting linker, which is a single-stranded DNA consisting of the palindromic base sequence of SEQ ID NO: 2.

4. The translation frame-adjusting linker of claim 3, of which the 5'-terminal is phosphorylated.

* * * * *

SEQUENCE LISTING

```
<160> NUMBER OF SEQ ID NOS: 2

<210> SEQ ID NO 1
<211> LENGTH: 12
<212> TYPE: DNA
<213> ORGANISM: Artificial sequence
<220> FEATURE:
<223> OTHER INFORMATION: Synthesized oligonucleotide

<400> SEQUENCE: 1
gccggcgccg gc                                                    12

<210> SEQ ID NO 2
<211> LENGTH: 14
<212> TYPE: DNA
<213> ORGANISM: Artificial sequence
<220> FEATURE:
<223> OTHER INFORMATION: Synthesized oligonucleotide

<400> SEQUENCE: 2
gcccgggccc gggc                                                  14
```